United States Patent [19]

Straus

[11] Patent Number: 4,489,158

[45] Date of Patent: Dec. 18, 1984

[54] BINDING ASSAY FOR THE DETECTION OF MYCOBACTERIA

[75] Inventor: Eugene W. Straus, New York, N.Y.

[73] Assignee: Montefiore Hospital and Medical Center, Inc., Bronx, N.Y.

[21] Appl. No.: 421,956

[22] Filed: Sep. 23, 1982

Related U.S. Application Data

[62] Division of Ser. No. 146,294, May 5, 1980, Pat. No. 4,410,660.

[51] Int. Cl.³ .................... G01N 33/54; C12Q 1/04
[52] U.S. Cl. .................................. 435/7; 435/34; 435/863; 436/545
[58] Field of Search .............. 435/7, 34, 863; 436/516, 527, 528, 529, 530, 531, 532, 533, 539, 540, 541, 545; 422/61; 424/1

[56] References Cited

U.S. PATENT DOCUMENTS 4,205,058  5/1980  Wagner et al. .................... 436/500

FOREIGN PATENT DOCUMENTS 1430464  3/1976  United Kingdom .

OTHER PUBLICATIONS

Straus and Yarlow, "Radioimmunoassay for Tuberculin Purified Protein Derivative," Clinical Research, vol. 25, No. 3, A382, Apr. 1977.

T. Daniel and P. Anderson Am. Rev. Resp. Dis. vol. 117, 1978 pp. 533–539.

K. Gupta and S. Landi, Can. J. Microbiology vol. 24, No. 10, 1978 pp. 1242–1249.

Chemical Abstracts, vol. 88, 1978, Abstract 88:150381f.

Primary Examiner—Thomas G. Wiseman
Assistant Examiner—Jayme A. Holeatt
Attorney, Agent, or Firm—Anthony J. Casella; Gerald E. Hespos

[57] ABSTRACT

A method for detecting the presence of Mycobacteria in a fluid or tissue which comprises mixing the fluid or tissue containing a secretory product of Mycobacteria with a complex of a tracer-containing molecule and a binding macromolecule having reversible binding affinity for the tracer-containing molecule and detecting the tracer-containing molecule, wherein the tracer-containing molecule is a charcoal-adsorbable protein from *Mycobacterium tuberculosis* which has a molecular weight of 20,000–30,000 and which is immunochemically stable from 4° C. to 250° C. and has a pH range from 3.0 to 9.0. The method is particularly applicable to the detection of infectious tuberculosis in humans and determining the antibiotic sensitivity of infecting Mycobacteria.

29 Claims, 5 Drawing Figures

BINDING ASSAY FOR THE DETECTION OF MYCOBACTERIA

This is a division, of application Ser. No. 146,294 filed May 5, 1980 U.S. Pat. No. 4,410,660.

BACKGROUND OF THE INVENTION

1. Field of the Invention

The present invention relates to a binding assay for the detection of Mycobacteria in fluids. In a preferred embodiment, the invention relates to a method for the diagnosis for tuberculosis in humans.

2. Description of the Prior Art

Mycobacteria cause a wide variety of infections both in human and non-human animals. For example, *M. tuberculosis* is the causative organism of human tuberculosis; it was isolated and identified in 1882. *M. leprae* is the cause of Hansen's disease and *M. lepraemurium* is the cause of a leprosy-like disease in rats. *M. bovis* is the cause of cattle infections, and it, like M. tuberculosis also causes infections in man. *M. avium* is strongly pathogenic for fowl, yet not pathogenic for man. Other tubercle bacilli of the Mycobacterium genus are the so-called cold-blooded animal type and the saprophytic types. The latter two are not pathogenic for man.

*M. tuberculosis* is an almost exclusive parasite of man. It is responsible for over 90% of all cases of tuberculosis, whereas the bovine type produces tuberculosis in man through ingestion of infected beef, or milk from an infected cow. Although infection from *M. bovis,* generally manifested as tuberculosis of the bones or lymphatic system, has been largely eliminated as a source of human infection in the United States as a result of Governmental inspection of meats, infection due to *M. tuberculosis* is still a major world health problem. According to the World Health Organization, there were 15 to 20 million infectious cases of tuberculosis in the world in 1967. The report for 1967 also stated that two to three million deaths due to tuberculosis occur each year with 80% of the deaths in developing countries. (Pelczar, Jr. and Reid, "Microbiology", Third Edition, McGraw-Hill (1972), p. 78). In 1976, more than 32,000 new cases were reported in the United States alone. Eradication of tuberculosis in man and similar infections in non-human animals is therefore still of utmost significance in the United States and the rest of the world.

Detection of actively growing Mycobacteria in human and non-human animals has been carried out in the prior art by classical staining and culture methodology. Mycobacteria are difficult to stain with the usual microbiological dyes, but they stain readily by the Ziehl-Neelsen technique (initial staining with basic fuchsin washed with acid and alcohol). Probably because of the high fat content of the organisms, they are not decolorized by the acid-alcohol and therefore have been termed acid-fast organisms. The requirement for isolation and culture of Mycobacteria from relatively inaccessible organs coupled with the slow multiplication rate of the tubercle bacillus, presents a problem for rapid diagnosis. In fact, since tuberculosis is a chronic baterial disease, advancing slowly, the primary infection may go unnoticed until a chance x-ray reveals lung lesions.

The demonstration of tubercle bacilli in body discharges—sputum, gastric contents, spinal fluid, urine, etc.—is the final proof in corroboration of clinical diagnosis. Laboratory methods include microscope examination of stained samples for the presence of bacilli, planting the suspected material on suitable culture media, and animal innoculation with concentrated sputum or other material in which the organisms may be found.

Another diagnostic method is the use of the tuberculin test. The test is performed by injecting intracutaneously small amunts of tuberculin, a purified protein derivative from cultured tuberculosis bacilli. A positive test is indicated by an inflammatory reaction at the site of injection within 48 hours. A positive tuberculin test, however, is not necessarily an indication of an existing infection in adults for it may simply mean that they once harbored the bacilli or some non-pathogenic Mycobacterium or an atypical *M. tuberculosis*. In children, a positive test is usually an indication for treatment. X-ray examination is generally employed to corroborate pulmonary infection. However, at present only identification of Mycobacteria in cultures of clinical specimens can be considered proof of active disease. Alternative and somewhat more efficient methods for rapid detection of growing Mycobacteria, especially for the rapid diagnosis for tuberculosis, have been proposed in the prior art. Thus, Odham et al (J. Clin. Invest. 63:813–819 (1979)), have demonstrated the presence of tuberculostearic acid in sputum from patients with pulmonary tuberculosis by selective ion monitoring.

Straus and Yalow (Clinical Research, Volume 25, No. 3, April 1977, A384) describe a radioimmunoassay (RIA) procedure for the detection of tuberculin purified protein derivative (PPD) shed into culture media by growing Mycobacterium tuberculosis. In this procedure, antisera were raised in guinea pigs by repeated subcutaneous injection of PPD (a readily available commercial product). PPD was iodinated with $^{125}$I and analysis of the radiolabeled PPD by Sepharose 6B column chromatography yielded a peak of radioactivity in the void volume (VVP) which was used as a tracer in RIA. Separation of the antibody-bound and free tracer was achieved by precipitation with rabbit anti-guinea pig $\gamma$-globulin. This radioimmunoassay is not useful, however, for the detection of *M. tuberculosis* or any other Mycobacterial species which are actively growing in an animal host such as a human or non-human infected animal. The Straus and Yalow assay (as described in the last two lines of the Abstract) was not sensitive enough to be employed for the rapid and direct identification of *M. tuberculosis* in biological fluids. The void volume peak (VVP) is generally too unstable to provide suitably labeled antigens and has the further disadvantage that precipitation with anti-guinea pig globulin is necessary to separate free from bound labeled antigens, since the VVP does not absorb on to charcoal.

A need, therefore, exists for a highly sensitive, rapid and efficient method for the detection of actively growing Mycobacteria in human and non-human animals. More particularly, a need exists for a rapid diagnostic method for the many different forms of tuberculosis in humans.

SUMMARY OF THE INVENTION

It is therefore an object of this invention to provide a method for the detection of actively growing Mycobacteria in human and non-human animals.

It is another object of the invention to provide a diagnostic method for tuberculosis in humans.

Still another object of the invention is to provide a binding assay method for the detection of Mycobacteria in animals by detecting secretory products of Mycobacteria in the biologic fluids of said animals.

Other objects of the invention are to provide a method for studying Mycobacterial growth and to provide a method for determining the sensitivity of Mycobacteria to the action of antibiotics.

Yet another object of the invention is to provide a radiolabeled tuberculoprotein derived from Mycobacterium tuberculosis which is heat stable and charcoal-adsorbable.

A further object of the invention is to provide a process for the preparation of the aforementioned radiolabeled tuberculin purified protein derivative.

Still a further object of the invention is to provide a diagnostic kit useful for the diagnosis by binding assay methodology of tuberculosis in humans.

These and other objects of the invention, as will hereinafter become more readily apparent, have been attained by providing:

A method for detecting the presence of Mycobacteria in a fluid or tissue which comprises:

mixing said fluid or tissue, containing a secretory product of Mycobacteria with a complex of a binding macromolecule and a tracer-containing molecule, and detecting said tracer-containing molecule;

wherein said tracer-containing molecule is a heat stable, charcoal-adsorbable protein purified from *Mycobacterium tuberculosis* which has a molecular weight of 20,000–30,000; preferably 24,000 Daltons.

Another object of the invention has been attained by providing a charcoal-adsorbable protein purified from *Mycobacterium tuberculosis* with a MW of 20,000–30,000, preferably 24,000 Daltons, which is immunochemically stable from 4° C. to 250° C. and over a pH range from 3.0 to 9.0, and which has well-defined mobility characteristics on starch gel electrophoresis.

Still another object of the invention has been attained by providing a method of preparing a tracer-containing protein purified from *Mycobacterium tuberculosis* which comprises:

labeling a mixture of tuberculoproteins isolated from the growth media of *Mycobacterium tuberculosis;* purifying from said mixture of labeled tuberculoproteins a labeled heat-stable, charcoal-adsorbable protein having a molecular weight of 20,000–30,000, preferably 24,000 Daltons.

Yet another object of the invention has been attained by providing a method of preparing a tracer-containing protein as described hereinbefore, wherein the purification is carried out by chromatographing a mixture of labeled tuberculoproteins isolated from the growth media of *M. tuberculosis* on beads of dextran cross-linked with epichlorohydrin, having a fractionation range for peptides of 3,000–80,000 and fractionating from said chromatographic step a purified, heat-stable, charcoal-adsorbable protein having a MW of 20,000–30,000.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows the gel chromatography of $^{125}I$ tuberculoproteins on a Sephacryl S200SF column. The most immunoreactive fraction is denoted as (A). See Example 1;

FIG. 2 shows the rechromatography of fraction (A) from FIG. 1, on a Sepharose 6B column. The most immunoreactive fraction is denoted as (B). See Example 1;

FIG. 3 shows the rechromatography of fraction (B) from FIG. 2 on a Sephadex G75. The most immunoreactive fraction is denoted as (C);

FIG. 4 shows a standard curve for the radioimmunoassay of the tuberculoprotein. Dilutions of autoclaved PPD and autoclaved culture medium are superimposable on the dilution curve of authentic standard; see Example 1.

FIG. 5 shows the starch gel electrophoresis of the purified protein from *M. tuberculosis* having a MW 24,000. Conditions:

Borate Buffer, pH 8.6, 80 volts, 12 hours. Legend: Alb: albumin; BpB: Bromophenol Blue.

DESCRIPTION OF THE PREFERRED EMBODIMENTS

The present invention has succeeded in providing a highly sensitive, fast, safe and effective method for the detection of Mycobacteria in the biological fluids of human and non-human animals. The present inventors have discovered that when Mycobacteria infect an animal host, the Mycobacteria secrete, into the physiological fluids of said host, tuberculoproteins which can be detected by a highly specific binding assay. This is the first time that the presence of an infecting microorganism has been detected by measuring the amount of a secretory product of said microorganism in the biological fluids of the host. It is quite likely that all metabolically active bacteria secrete non-toxic species and strain-specific products. However, until this invention, the primary identification of such materials has not commonly been exploited as a diagnostic method. The development of a binding assay for a Mycobacterial secretory product thus represents a new diagnostic approach.

The essence of the invention relates to the preparation of a stable, tracer-containing protein from *M. tuberculosis* capable of being used in a binding assay for the secretory products of Mycobacteria. This stable, tracer-containing protein is prepared from a readily available tuberculin purified protein derivative (PPD) obtainable from Connaught Laboratories Limited, Toronto, Ontario, Canada. The preparation of PPD is fully described in Gupta and Landi (Canadian Journal of Microbiology, 24: 1242–1249 (1978)) and Landi, S., (Appl, Microbiology, 11: 408–412, 1963). The description and preparation of PPD has also been published in Landi, S. et al in: Proceedings of Third Conference of Evaluation of Procedures for Tuberculin Testing, U.S. Dept. of HEW; Atlanta, Ga., May 4, 1971 (39–47), and Landi, S., et al, Tubercle, 59: 121–133 (1978). Any acid or salt precipitated mixture of tubercular proteins isolated from the growth media of actively growing Mycobacteria can be used as the starting material for the preparation of the tracer-containing molecule. PPD is but one of the preferred examples of such mixture of tubercular proteins.

The mixture of tubercular proteins, preferably PPD, is labeled in order to prepare the tracer-containing molecule. Any label useful in binding assays, particularly in radioimmunoassays, can be used. Tracer molecules can be divided into two types: those with an internal label and those with an external label. With an internal label, an existing atom in the ligand molecule is replaced by a radioactive isotope of that atom (e.g., $C^{14}$ for $C^{12}$, $H^3$ for $H^1$). With an external label, an atom or atoms of a radioactive isotope (e.g., $I^{131}$ or $I^{125}$) are substituted for an existing atom on the ligand molecule; to achieve stability, a covalent link is established between label and ligand. A tracer with an external label such as $I^{125}$ is not identical with the unlabeled ligand, but its behavior is practically indistinguishable from the latter. Both the internal or external label methodology can be used in the present invention. The most preferred method is that of using an external label, most preferably radioactive iodine. It is known that iodine can be substituted into the aromatic side-chain of tyrosine residues, as well as other amino acids such as histidine. Many procedures have been described for iodination, and they can all be used in the present invention. The following methods of iodination have been described:

1. Chloramine T technique (Greenwood, F. C., et al, Biochemical Journal, 89, 114 (1963)). The procedure is simple since all that is required is mixing a solution of the protein mixture, sodium iodide having radioactive iodine and chloramine T; the reaction is terminated by the addition of a reducing agent, preferably sodium metabisulfite.

2. Iodine monochloride technique (McFarlane, A. S., Nature 182, 53 (1958)). A solution of iodine monochloride is mixed with solutions of the radioactive isotopes and the protein mixture.

3. Chlorine and hypochloride technique (Redshaw et al, Journal of Endocrinology, Vol. 60, 527 (1974)).

4. Lactoperoxidase (Marchlonis, J. J., Biochemical Journal, 113, 299 (1969)). In this technique enzymatic iodination using lactoperoxidase in the presence of a trace of hydrogen peroxide is carried out on the protein mixture. The advantage is that the protein mixture is not exposed to high concentrations of a chemical oxidizing agent such as chloramine T. Furthermore, a reducing agent is not required since simple dilution will stop the reaction. Alternatively, the lactoperoxidase can be attached to a solid phase and removed by centrifugation. The preparation of reagents and conditions for the reaction itself are more technically demanding than those for the chloramine T procedure.

5. Electrolysis (Rosa, U., et al, Biochem. Biophys., Acta, 86, 519, (1964)). This technique involves the use of iodide in the reaction mixture being converted to reactive forms by the passage of an electric current.

6. Iodine vaporization. A mixture of chloramine T and isotopic sodium iodide yields gaseous iodine. The reaction is carried out in a gas-tight outer vessel in which is a smaller inner vessel containing a solution of a protein mixture; the reactive iodine vapor diffuses into the solution.

7. Conjugation labeling technique (Bolton, A. E., et al, Biochemical Journal, 133, 529 (1973)). In this procedure the iodine is first coupled to an appropriate carrier "handle" containing a phenol or imidazole group for iodination, and an amine for coupling to the ligand or its derivative.

For a general description of all of these labeling techniques see Chard: "An Introduction to Radioimmunoassay and Related Techniques", North Holland Publishing Company, Amsterdam, N.Y., Oxford, First Edition, 1978.

Labels other than radioactive labels can, of course, be used since they are well known in generalized binding assay techniques. Thus, for example, alternatives to isotopic labels may be: (a) chromophoric labels, such as fluorescent, ultraviolet-absorbing or visible light-absorbing labels: These are advantageous because of their long shelf life and absence of radiation effects; (b) Enzyme labels (Enzyme-linked immunoabsorbent assay ("Elisa")): Since specific enzymes can be coupled to other molecules by covalent links, a highly specific enzyme may be covalently reacted with the partially purified Mycobacterial protein mixture and the resulting "tracer-containing molecule" can be purified to obtain the required fraction for use in the binding assay (see Chard, supra, at 374–375); alternatively, pure protein can be linked to enzyme (see Engvall et al, J. Immunol. 109, 120 (1972)); (c) other tracers such as free radical labels or bacterial phase labels could also be used in the present invention (see Chard, supra, at 376). The most preferred method of preparing a tracer-containing molecule is radiolabeling with radioactive iodine.

Once the labeled protein mixture has been prepared by any of the aforementioned techniques, the desired tracer-containing molecule is purified therefrom, by an appropriate purification method, including chromatography. Two gel filtration chromatographic techniques and a silica gel technique can be described here as examples:

1. One-step Gel Filtration Technique. The labeled mixture is fractionated on a chromatographic column containing beads of dextran cross-linked with epichlorohydrin (known as Sephadex) and having a fractionation range for peptides of 3,000–80,000. After elution in an appropriate buffer and fractionation, the peak containing a protein fraction having a molecular weight of 20,000–30,000 preferably about 24,000 Daltons is isolated and utilized. The tracer-containing purified protein from M. tuberculosis thus isolated easily adsorbs on charcoal, and shows a high degree of stability. It shows a remarkable degree of heat stability, remaining immunochemically intact over a range of 4° C.–250° C. This can be ascertained by demonstrating that an autoclaving treatment at 250° C. does not change the immunochemical specificity of the protein (see FIG. 4). The protein also shows a high degree of acid stability, being immunochemically unchanged over the range of pH 3.0–9.0. It has a shelf life of several months, at pH 8.0–9.0, 4° C.-room temperature.

The final product can also be characterized by its characteristic behavior on starch gel electrophoresis. Using this electrophoretic technique in borate buffer, pH 8.6 at 80 volts for 12 hours, the $^{125}I$-tracer-containing molecule comigrates with bovine serum albumin.

In contrast, the VVP material described by Straus and Yalow (Clinical Research, Vol. 25, No. 3, A384, 1977) is non-charcoal adsorbable, has a different gel electrophoresis pattern, and is only stable for a few hours. In addition, since it is isolated from the void volume peak of a Sepharose 6B column, the molecular weight is in the millions, and not about 24,000 as the protein of the present invention. The materials are therefore very different.

2. Three-stage Gel Filtration Technique. In this purification, the labeled protein mixture prepared above, is first fractionated on a gel permeation chromatographic column of allyl dextran cross-linked with N,N'-methylene-bis-acrylamide, having a MW fractionation range for proteins of $5\times10^3$–$2.5\times10^5$. This material is commercially known as Sephacryl S200. The most immunoreactive peak is isolated and refractionated on a gel chromatographic column of neutral agarose beads, which is substantially free of charged groups, and has a protein fractionation range of $10^4$–$4 \times 10^6$. This material is commercially available and known as Sepharose 6B. The refractionated material having the highest immunoreactivity is thirdly added to a gel chromatographic column of dextran beads crosslinked with epichlorohydrin (Sephadex G75, supra), having a MW fractionation range for proteins of 3,000–80,000. The material having a molecular weight of 20,000–30,000, preferably 24,000 Daltons, which is heat stable and charcoal-adsorbable is isolated and used. This material is essentially similar to the material purified by the one-step technique.

In both the one-step and three-step techniques, the appearance of purified protein can be readily followed by the use of the incorporated label.

3. Silica Gel Technique. Purification or repurification can also be performed by adsorption and elution from silica gel, where adsorption is carried out at pH 1.0–4.0, preferably 2.0–3.0, and elution at pH 7.0–9.0, preferably 8.0–9.0.

The aforementioned three chromatographic techniques, as well as any other purification techniques, can be operated in any buffer normally used therefor. Examples of such buffers are phosphate, borate, tris, veronal, glycine, histidine, PIPES, HEPES, and the like, at concentrations depending on the desired buffer capacity, easily determinable by one skilled in the art, normally 0.01M-1.0M.

The tracer or label-containing purified Mycobacterial constituent thus prepared, can be used successfully in any of the well known competitive binding assays, of which radioimmunoassay is but one example. With this stable, charcoal-adsorbable tubercular protein from *M. tuberculosis* as tracer, it is possible for the first time to detect the presence of Mycobacteria, by detecting minute amounts of Mycobacterial secretory products which are shed into fluids or tissues. In order to carry out a competitive binding assay, preferably a radioimmunoassay, it is necessary to provide a binding macromolecule which has reversible affinity for the tracer or label-containing molecule, and for Mycobacterial secretory products. Such a binding macromolecule is most generally an antibody raised against the Mycobacterial secretory product. It is also obvious that the binding macromolecule, preferably antibody, should as far as possible be directed only to the Mycobacterial secretory proteins which the assay is intended to measure, not to a wide variety of similar materials which would interfere with specificity.

The preparation of anti-sera in animals is a well-known technique (see for example Chard, supra, pp. 385–396). The choice of animal is usually determined by a balance between the facilities available, and the likely requirements in terms of volume of the resulting antiserum. A large species such as goat, donkey and horse may be preferred, because of the larger volumes of serum readily obtained, however, it is also possible to use smaller species such as rabbits or guinea pigs which often have high titer antisera. Usually, subcutaneous injection of Mycobacterial PPD coupled to guinea pig albumin and emulsified in Freund's complete adjuvant is sufficient to produce anti-PPD antisera. The detection of appropriate antibodies can be carried out by testing the antisera with appropriately labeled tracer-containing molecules. Fractions that bind tracer-containing molecules are then isolated and further purified if necessary.

It is of course possible to use other than antibodies as the binding macromolecule. The use of cell receptors specific for Mycobacterial proteins, or of any circulating binding proteins equally specific for Mycobacterial proteins can be used.

The general competitive binding assay techniques useful for the detection of minute amounts of organic molecules such as hormones, proteins, antibodies, and the like are well known in the art (see Chard, supra). Any of these competitive binding assay techniques can be used for the purposes of the present invention.

A small amount of the fluid or tissue sample suspected of containing the Mycobacterial secretory product is incubated with a complex of the labeled tracer-containing purified constituent and the binding macromolecule therefor, preferably an antibody raised against Mycobacterial proteins. Any fluid or tissue sample derived from a source suspected of containing Mycobacteria can be used. This includes the physiological fluids of human and non-human animals, such as urine, blood, spinal fluid, and the like.

Apart from humans, the most common animals which are subject to Mycobacterial infections are bovines, fowl and rabbits. However, other media may be contaminated with Mycobacteria or their secretory products: these might include liquid sources such as suspected contaminated milk, water or other consumable or non-consumable liquids. All that is required of the liquid or tissue being examined is that it be capable of containing Mycobacterial secretory products shed thereinto.

Once the incubation of the test sample with the complex of the binding macromolecule and tracer-containing molecule is complete, it is necessary to determine the distribution of the tracer-containing molecule between the free and the bound form. Usually, but not always, this requires that the bound fraction be physically separated from the free fraction; a variety of techniques can be used for that purpose. All of the techniques exploit physical-chemical differences between the tracer-containing molecule in its free and bound form. The general available methodologies have been described by Yalow (Pharmacol. Rev. 28, 161 (1973)). These techniques include adsorption of free antigen to solid phase material, such as cellulose, charcoal, silicates or ion exchange resins; precipitation of antigen-antibody complexes by second antibody; salting out techniques or organic solvents; adsorption or complexing of antibody to solid phase material; electrophoretic separation on cellulose, starch gel or polyacrylamide gel, and the like. (See also Chard, supra, pp. 405–422). Suitable organic solvents include ethanol, dioxane, polyethylene glycol, trichloroacetic acid, a solution of sodium sulfite, and a solution of ammonium sulfate.

The choice of a technique depends on the speed, simplicity, applicability and cost. It is a simple matter of choice for anyone skilled in the art and therefore the generalized techniques will not be described in further detail.

Particularly preferred among the aforementioned techniques are adsorption methods, double-antibody methods and solid phase systems.

In adsorption methodology, the non-specific adsorption of proteins to particle surfaces is used as a method for the separation of bound and free tracer-containing molecules. This procedure depends on the fact that only the tracer-containing molecules and not the binding macromolecules or bound complexes have the adsorption property. The most preferred adsorption procedure which is highly useful in the present case, is adsorption on charcoal or silicates. The most commonly used of the available charcoals are the Norit range (Norit SX1) with a maximum particle size of 63 μm. Considerable batch-to-batch variation may be found with these and it should never be assumed that the material in bottles with apparently identical labels will behave identically in any assay. Each batch, therefore, has to be carefully tested before it is put into routine use. Particular silicates have adsorptive properties which advantage is taken for the separation. Materials employed may include talc, microfine precipitated silica ($Q_{uso}$) and Fuller's earth.

"Double" or "second" antibody methods depend on the precipitation of the bound complex with an antibody directed to the macromolecule. The second antibody is specific to the γ-globulin of the species in which the first antibody was raised, for example if a guinea pig anti-PPD serum is used in the primary reaction of an assay for Mycobacterial secretory products, an atiserum to guinea pig γ-globulin raised in a goat may be used for the separation step. Although most commonly used in radioimmunoassays, this concept can be applied to any binding macromolecule for which an antiserum is available. Separation by this technique requires a relatively large concentration of second antibody and a correspondingly large amount of the species of γ-globulins of which the first antibody forms a part must be included; for this purpose, a second antibody system always involves the addition of carrier protein, either whole serum or γ-globulin from the species in which the first antibody was raised. The use of second-antibody techniques suffers from two important practical disadvantages. The first is that it requires an additional period of incubation which may range from one to twenty-four hours and can, therefore, considerably extend the time required to complete the assay. A second practical disadvantage is that of reagent supply. A new second antibody requires careful evaluation and of those tested few will turn out to be completely satisfactory. Relatively high concentrations are required and the product of one animal is only sufficient for a limited number of assays. Second-antibody systems are therefore also quite expensive. The use of coupling of the second antibody to an insoluble matrix such as cellulose is more economical and efficient and has been described by den Hollander et al. (Kirkham et al "Radioimmunoassay Methods" (1971) p. 419).

Solid phase systems in general have been increasingly utilized in recent years. When the binding macromolecule is covalently coupled to an insoluble support, then both it and the bound complex can readily be separated from the soluble free fraction. A wide variety of solid-phase supports have been described, which include particles of dextran and cellulose, and continuous surfaces such as polystyrene or polypropylene discs, or the walls of plastic or glass tubes. Plastic surfaces exhibit adsorptive properties, and simply exposing such surface to an appropriate dilution of the anti-PPD antiserum will lead to the attachment of a proportion of the antibody molecules thereon. The bond is probably ionic or hydrophobic and not covalent. Covalent bonding, however, can be readily obtained by the incorporation of cross-linking agents such as glutaraldehyde and other agents in the antibody solution used for the coating.

Coated tube systems offer great convenience in the actual performance of assays and the technique can be widely use in commercial kits. In one preferred embodiment, the anti-PPD antibody is covalently attached to the inside of a test tube and tracer-containing molecule is also incorporated in the tube. A single addition of a sample of fluid or solution of tissue being tested is then added to the test tube. After incubation, the contents of the tube are emptied and the tracer is detected by standard methodology.

The binding macromolecule can also be attached to a particulate solid phase by any one of a number of techniques designed to yield a covalent link between the protein and the particles, such as for example diazotization or cyanogen bromide activation. The resulting material is then extensively washed to ensure that no free γ-globulin molecules remain. Alternative approaches include the use of antibody entrapped in the interstices of a polyacrylamide gel or covalently bound to magnetic particles (polymer-coated iron oxide). With the latter system, mixing and separation can be simply achieved by the application of a magnetic field.

An alternative binding approach to the detection of Mycobacterial secretory product from fluids or tissues is by using the recently developed latex particle agglutination technique. This technique does not involve the use of a tracer or label-containing ligand having reversible affinity for the binding macromolecule but rather the use of the unlabeled ligand itself. See for example, Sawai et al, U.S. Pat. No. 4,118,192 or Hoffmann-LaRoche, British Pat. No. 1,384,399. The techniques described in these two patents are readily applicable to the specific process of the present invention. In these techniques, antibody raised against PPD is supported on an insoluble carrier particle, usually a latex particle, thus sensitizing the insoluble carrier particle. The supported anti-PPD is then reacted with the sample suspected of containing the Mycobacterial secretory tubercular protein product. The sensitized latex agglutinates to a degree which is proportional to the amount of secretory product present in the fluid or tissue. The agglutination is then followed by irradiating the resulting reaction mixture with light having a wave-length in the range of 0.6–2.4 microns. The determination of absorbance can be performed with a spectrophotometer similar to that used in near infrared spectrometry. Polystyrene latexes or styrene butadiene-latexes can readily be used; however, other particles such as dispersed coccal bacteria, cell membrane fragments, microparticles of inorganic oxides such as silica, silica alumina and alumina or finely pulverized minerals, metals and the like are also readily useable. These latex agglutination techniques not only make it possible to determine low concentrations of Mycobacterial secretory product, but enables the determination of such secretory products in trace amounts and with comparable specificity to those of the radioimmunoassay methodology. The amount of secretory Mycobacterial product can be determined by measuring the absorbance as described above, or alternatively by measuring the rate of reaction, or the reaction time required for the absorbance to reach a prescribed value. The Sawai et al methodology is also applicable in the inhibition-of-agglutination mode. In this mode, latex particles are coated with protein purified from M. tuberculosis having a molecular weight of about 24,000, which preparation has been extensively discussed above. These particles are then incubated with anti-PPD. The so-formed complex is mixed with test fluid or tissue suspected of containing Mycobacterial secretory products. If the test sample contains secretory products, the latter will compete for the antibody binding sites and inhibit the agglutination of the antigen-covered latex particles. The protein of molecular weight 24,000 used for the radio-binding assays described previously need not, in the latex techniques, contain any radioactive label or tracer. It may be useful, however, for simple purposes of purification and isolation of this protein, to proceed as indicated previously and incorporate a label of tracer.

When radioimmunoassay is utilized as the mode of detection of Mycobacterial secretory products, and after incubation of the test sample with the antibody-tracer-containing molecule complex and separation of the tracer-containing molecule, it is necessary to detect the tracer by some physical or chemical means. When the tracer is the preferred radioactive iodine, scintillation counting is the method of choice. Radioactive iodine is a γ-ray emitter and therefore intimate contact between the isotope and the scintillator is unnecessary. The scintillator in these cases usually consists of a crystal of sodium iodide coated with thallium, usually formed as a well; as the radiation strikes the molecules making up the crystal lattice, ionization occurs and results in a light flash which is then detected by the photo multiplier. If the radioisotope used for labeling is $C^{14}$ or $H^3$, liquid scintillation is appropriate to detect β-particles.

The data obtained from tracer binding assays can be plotted in any of a variety of standard plots. A commonly used method is a plot of percent bound, or the ratio of bound to free ligand (B/R) as a function of the standard concentrations of secretory product. The inverse ratio of free to bound (F/B) can also be used. Many workers employ a semilogarithmic plot of percentage tracer bound against the log of concentration of unlabeled secretory product. The choice of plot is very much a matter of personal taste or experience of the individual workers. Generally, it is necessary to prepare a series of standards containing different concentrations of secretory protein, such as PPD. A standard curve is then prepared which can be used for any subsequent radioimmunoassay determinations. The validity of the assay is independent of the choice of plot employed.

The methodology of the present invention can be used to detect a wide variety of Mycobacterial species. Although material derived from *M. tuberculosis* reacts most strongly, there is wide cross-reactivity with other pathologic Mycobacterial species. Immunoreactive material can be detected in culture media and test samples of all disease producing Mycobacterial species and no reactivity is detected in media or test samples from diverse bacterial or fungal species. The cross-reactivity observed with the assay is consistent with the amino acid compositions of tubercular proteins from a variety of Mycobacterial species, which compositions have recently been found to be very similar (Landi, S. et al, Ann. Sclavo 13, 862–883 (1973)). This pattern of cross-reactivity appears favorable since it allows identification of Mycobacterial infection caused by a variety of species. The efficacy of the method can also be enhanced by working with contaminated specimens containing greater numbers of Mycobacteria. The availability of tubercular protein derived from other species offers the possibility of developing additional assays for greater diagnostic specificity. In this respect, it is possible to carry out a preliminary screening for the general presence of Mycobacteria in the test sample, followed by a more specific determination for the type of species of Mycobacteria in the test sample. If species identification were desired, the sample could be assayed in several similar assay systems each employing antisera with enhanced specificity for a given species of Mycobacteria. Among the detectable Mycobacterial species are *M. leprae, M. lepraemurium, M. tuberculosis, M. bovis, M. marinum M. avium, M. Phlei, M. smegmatis, M. intracellulare, M. simiae, M-xeuopi M. kansasii, M. batti M. ofricanium, M. ulcerans* and the like.

Another very useful application of the method of the invention is in the determination of susceptibility of Mycobacteria to antibiotic substances. Drugs such as isoniazid, streptomycin, ethionamide, tetracyclines, rifampin, ethambutol, aminosalicyclic acid and pyrazinamide are commonly used in the treatment of tuberculosis. A quick method to ascertain whether the infecting Mycobacteria is susceptible to any of these, is to determine the presence of immunoreactive secretory products of bacteria which are growing in the presence of the drugs.

The techniques and materials of the present invention for the detection of Mycobacterial secretory product in test samples or tissues can be readily automated. A noteworthy development in the field of automated radioimmunoassay is the recent patent of Brooker et al, U.S. Pat. No. 4,022,577. Among the kits useful in the present invention are those of the general type described by Szczesniak, U.S. Pat. No. 3,899,298. Such kits comprise a carrier being compartmented to receive at least one, or at least two, or at least three or more, vials and to maintain said vials in closed confinement. A first vial may contain tracer- or label-containing ligand molecules such as for example the radiolabeled protein of molecular weight 20,000–30,000, preferably 24,000 Daltons. Another vial may contain anti-PPD antibodies raised in an appropriate animal. These materials may be in the freeze-dried state or suspended in a buffer solution. When in a freeze-dried state, the buffer solution may be in a third vial. Alternatively, the complex of anti-PPD and tracer-containing molecule may be present in one vial and buffer solution which may be added at the time of testing may be present in another vial. Alternatively, the first vial may be a test tube being covalently coated at the inner surface thereof with antibodies, e.g., anti-PPD. A second vial may be the tracer-containing purified Mycobacterial protein of MW 20,000–30,000, in the presence or absence of buffer. At the time of test, the buffer suspension of tracer-containing molecule is added to the antibody-coated test tube and a drop or two of test sample containing the suspected Mycobacterial secretory products is added to the test tube. Alternatively, the first vial may be a test tube coated at its inner surfaces with anti-PPD and containing in complexation therewith the tracer-containing molecule. At the time of testing, the addition of the suspect test sample is then sufficient to carry out the methodology. Other vials in the carrier may contain the elements necessary for the separation of bound and free tracer-containing ligand. Thus, such vials may contain charcoal, silicates, or second-antibodies useful in the "second-antibody technique" described previously. Any number of variations and permutations consistent with the various techniques described previously can be envisioned for the preparation of the kit. These are all matters of choice determined by the ease of handling, rapidity and efficiency of the testing. Other apparatus useful for the present invention are for example, the recently described "gamma stick", Schen, U.S. Pat. No. 4,135,884. Schen describes a test stick adaptable to be introduced into a test tube. The stick has a test portion adapted to be coated with antibody, in this case anti-PPD. The test tube contains antigen-containing solution. A variation of this technique is described in Bratu, U.S. Pat. No. 3,826,619, and is also readily applicable to the present invention. Another useful apparatus for the present invention is that of Updike, U.S. Pat. No. 3,970,429. Updike describes a syringe-like apparatus loaded with hydrophilic insoluble porous gel particles having binding macromolecules trapped therein. These binding macromolecules would be, for example anti-PPD. A fluid to be tested is introduced into the syringe by means of a plunger and contacts the gel particles whereby some of the binding sites of the binding macromolecules are occupied. This is followed by exposure of the gel particles to radioactive tagged tracer-containing material, followed by measurement of the radioactivity of the unbound or bound tagged material. The binding proteins or macromolecules in the gel particles are returned to the original state for reuse by treatment with acidic medium to affect detachment of the bound material, followed by washing to affect removal of the unbound material.

Having now generally described the invention, the same will be further illustrated by means of specific examples which are presented herewith for purposes of illustration only and are not intended to be limiting thereof, unless otherwise specified.

EXAMPLE 1

Iodination of PPD. PPD, (Landi, S. Appl. Microb., 11, 408–412 (1963)) was dissolved in 0.25M phosphate buffer pH 7.5 at a concentration of 3.5 mg per ml. Iodination was done using a minor modification of a chloramine T technique described in Berson, S. A. and Yalow, R. S. (General Radioimmunoassay, S. A. Berson and R. S. Yalow, "Methods in Investigative and Diagnostic Endocrinology", Part I, North Holland-Publishing Company, Amsterdam, 1973, pp. 84–120). For a typical iodination, approximately 200 MCi of $^{125}$I (commercially available) and 1.0 $\mu$g PPD were exposed to 52 $\mu$g of chloramine T for about 3 seconds before the addition of 96 $\mu$g of sodium metabisulfite. About 1 $\mu$l of the iodination mixture was added to plasma and applied to paper for chromatoelectrophoresis to monitor the extent of iodination.

Three Stage Chromatographic Purification. The iodination mixture was then placed at the top of a 1×50 cm Sephacryl S200 SF column and eluted with 0.02M barbital buffer, pH 8.6, containing 2% fetal bovine serum (standard diluent) at a flow rate of 10 ml per hour. A portion of each 1 ml fraction was then tested for binding to antiserum as described below under radioimmunoassay methodology. The Sephacryl S200 SF elution fraction which bound best to antibody was then placed at the top of a 1×50 cm Sepharose 6B column and eluted as described above. The Sepharose 6B elution fraction with the greatest immunoreactivity was then further fractionated on a 1×50 cm Sephadex G75 column and each fraction was again examined for binding to antibody.

Figure 1:
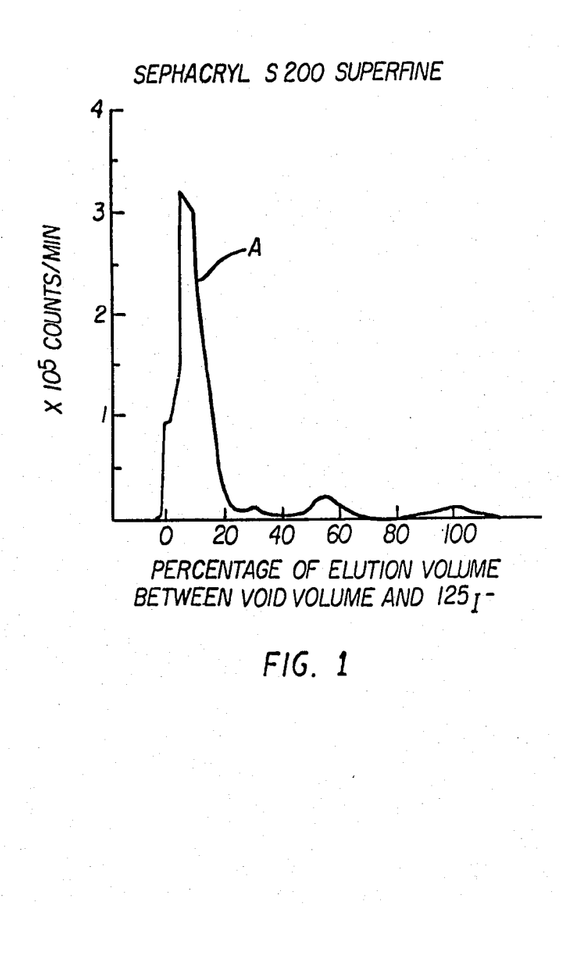
Figure 2:
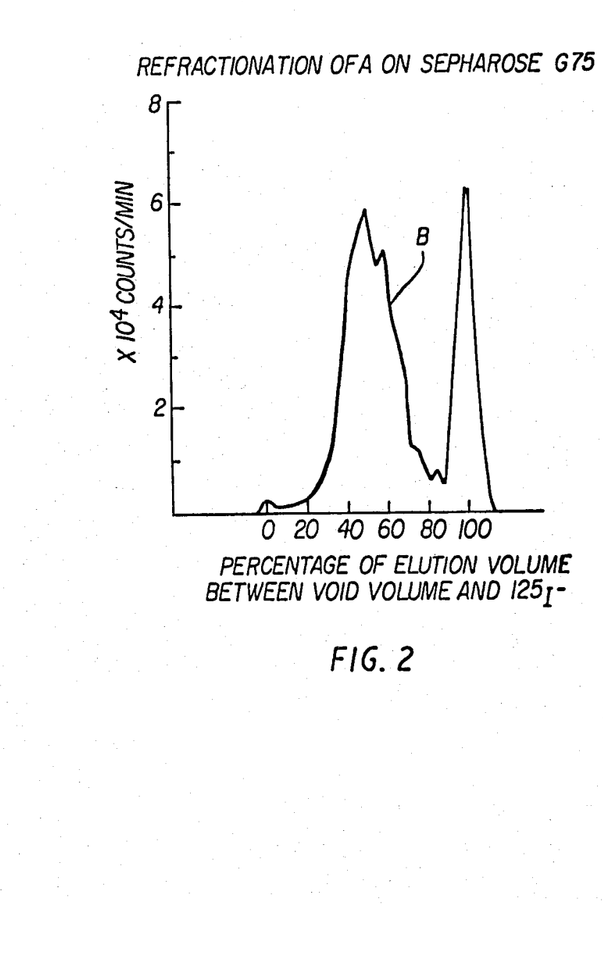
Figure 3:
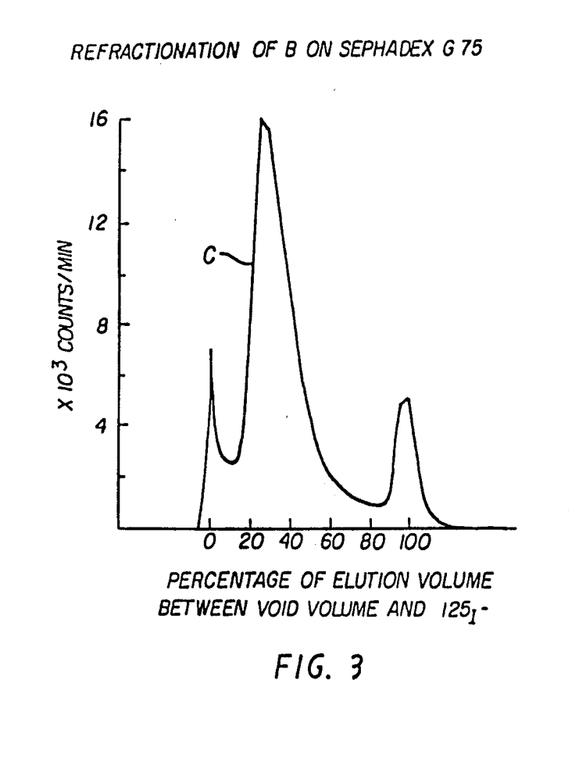

During iodination, greater than 75% of the $^{125}$I was incorporated into protein. However, since the commercial PPD is quite heterogeneous, a chromatographic pufification is required to obtain a fraction of $^{125}$I-PPD with optimal properties of binding to antibody. In the original fractionation on Sephacryl S200 SF, labeled PPD which combines to antibody is found in void volume eluates as well as in eluates corresponding to the major peak of radioactivity (FIG. 1). Fraction A in FIG. 1, on the descending limb of the major peak of radioactivity had a B/F ratio of 0.295 when used with a 1:2000 dilution of the antiserum. After testing, it was kept frozen for six weeks at $-20°$ C.; rechromatography on Sepharose 6B as described above (FIG. 2) was carried out. The best fraction, B, had a B/F ratio of 0.521 when tested under the same conditions as A. Deiodination, which had occurred during the six weeks storage, accounts for the late eluting peak. Rechromatography on fraction B on Sephadex G75 as described above, resulted in a major peak of radioactivity at about ¼ of the way between the void volume on the iodide peak (FIG. 3). Fraction C, on the ascending limb of the major peak, was the most immunoreactive (B/F ratio of 0.902). Thus labeled antigen can be stored for a period of several months and refractionated when needed for assay.

Silica Gel Purification Technique. The iodination mixture was adjusted to pH 2.3 before addition of 5 mg microfine precipitated silica (QUSO G32, commercially available). After mixing and centrifugation (3,000 rpm×15 min), the QUSO with adsorbed $^{125}$I-tuberculoprotein was washed twice with 3.0 ml distilled water adjusted to pH 3.2 with 0.1N HCl. The labeled material was then eluted from QUSO in 0.05 ml barbital, pH 8.6, containing 2% fetal bovine serum.

Preparation of the Antiserum. Six guinea pigs received a subcutaneous injection of about 1 mg of PPD coupled to guinea pig albumin by carbodiimide and emulsified in Freund's complete adjuvant. The guinea pigs were bled two weeks after immunization. Two of the six guinea pigs (GP4 and GP5) had circulating antibody which bound $^{125}$I-tuberculoprotein. Two weeks after a second injection, antibody titers were unchanged in GP4 and GP5. None of the other animals had significant titers.

Radioimmunoassay. Radioimmunoassay was performed in 1.0 ml of standard diluent containing GP5 plasma in a final concentration of 1:2000 and a tracer concentration of about 0.001 $\mu$Ci $^{125}$I-tuberculoprotein. PPD diluted to a concentration of 10 $\mu$g/ml in a standard diluent was used as standard. Unknown samples were generally assayed in final dilution of 1:40. Incubation was carried out overnight at 4° C. Separation of antibody bound and free $^{125}$I-tuberculoprotein was accomplished by addition of 0.2 ml of uncoated charcoal (Norit A) suspended in 0.02M barbital, pH 8.6, at a concentration of 100 mg per ml.

Culture technique. *M. tuberculosis* and *M. fortuitum* were cultured aerobically at 35° C. in Middlebrook 7H9 medium (commercially available). When cultures reached turbidity equal to McFarland nephelometer barium sulfate standard #1, a series of subcultures were made by removing 0.1 ml aliquots and adding these to tubes containing 5 ml of the same culture medium. Culture tubes were removed from incubation at 1 to 2 day intervals and autoclaved at 250° F. for one hour. These tubes were then stored at $-20°$ C. until assayed.

Nine fungi and ten bacterial species obtained from recent clinical isolates were cultured to luxurient growth at 35° C. in Middlebrook 7H9 medium. The organisms included the following: *Candida albicans, Cryptococcus neoformans, Fusarium species, Aspergillus* niger, *Aspergillus fumigatus, Norcardia asteroides, Torulopsis glabrata,* Mucor species, Syncephalostrum species, Pencillium species, *Listeria monocytogenes, Arizona hinshawii, Proteus mirabilis, Salmonella derby, Corynebacterium diptheriae, Providencia stuartii, Serratia marcescens, Yersinia enterocolitica, Streptococcus fecalis* and *Staphylococcus epidermidis.* The cultures were autoclaved at 250° F. for one hour and stored frozen until assayed.

Sputum samples from patients with pulmonary disease were decontaminated by 15 minute exposure to one volume of a solution containing N-acetyl-L-cysteine, 4% NaOH, and 2.9% Na citrate and cultured aerobically at 35° C. in Middlebrook 7H9 medium. Portions of the cultures were sampled between two and six weeks, autoclaved as described above and coded in the mycobacteriology laboratory prior to assay.

Figure 4:
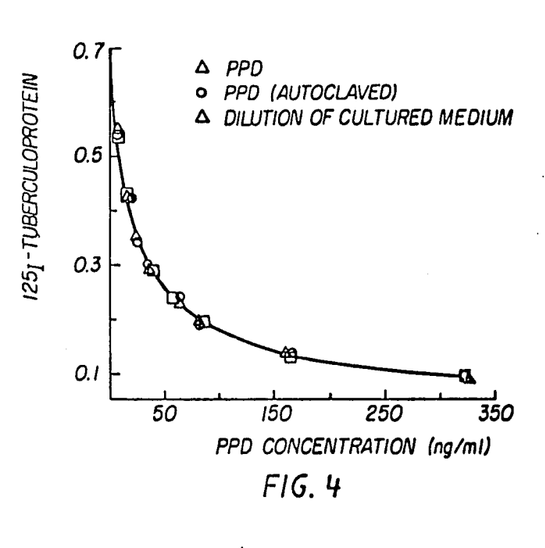
Figure 5:
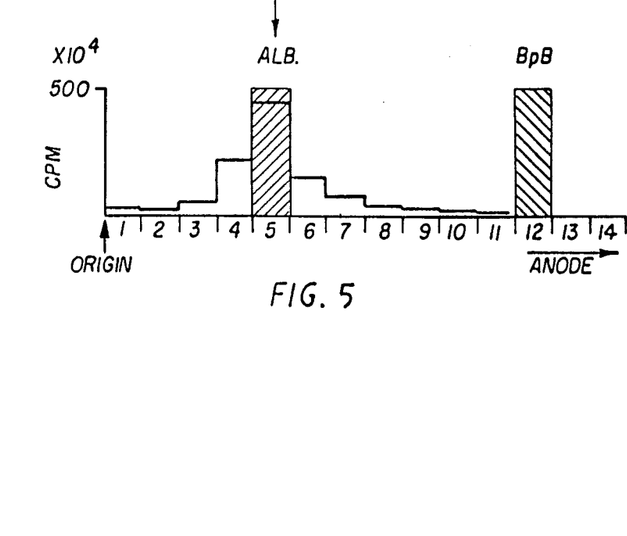

Results. A typical standare curve using the tracer-containing protein having a molecular weight of 24,000 Daltons as the labeled antigen is shown in FIG. 4. The range of minimal detectability (about 5 ng/ml) and the concentration required to produce half-maximal depression of the B/F ratio (about 25 ng/ml) are the same for autoclaved and unautoclaved PPD. The immunoreactivity in multiple dilutions of autoclaved Middlebrook 7H9 media containing *M. tuberculosis* is superimposable on this standard curve.

The concentrations of immunoreactive PPD in sputum cultures of patients with pulmonary infection are shown in Table 1:

TABLE I

Immunoreactive PPD Concentration in Sputum Culture from Patients with Pulmonary Infection.

| Patient | PPD (µg/ml) | Identification of Mycobacterium by Culture |
|---|---|---|
| 1 | 2.9 | *M. tuberculosis* |
| 2 | 23.6 | *M. tuberculosis* |
| 3 | 1.6 | *M. intracellulare* |
| 4 | 26.4 | *M. tuberculosis* |
| 5 | 2.0 | *M. tuberculosis* |
| 6 | 4.8 | *M. tuberculosis* |
| 7 | 25.1 | *M. tuberculosis* |
| 8 | 1.0 | *M. intracellulare* |
| 9 | 29.8 | *M. tuberculosis* |
| 10 | 0.6 | *M. intracellulare* |
| 11 | 0.6 | *M. intracellulare* |
| 12 | 23.0 | *M. tuberculosis* |
| 13 | 0.8 | *M. fortuitum* |
| 14 | 0.8 | *M. scrofulaceum* |
| 15 | 1.2 | *M. intracellulare* |
| 16 | 1.1 | *M. scrofulaceum* |
| 17 | 0.3 | *M. simiae* |
| 18 | ND* | |
| 19 | ND | |
| 20 | ND | |
| 21 | ND | |
| 22 | ND | |
| 23 | ND | |
| 24 | ND | |
| 25 | ND | |
| 26 | ND | |

*ND  not detectable

All cultures were maintained from 2-6 weeks. In no case were Mycobacteria identified by direct acid-fast smear of sputum. Immunoreactive tuberculoprotein was detected in all cultures in which Mycobacteria were identified. The concentrations were highest in cultures of *M. tuberculosis,* ranging from 2.0 to 29.8 µg/ml. In these cultures detectable immunoreactivity preceeded identification of *M. tuberculosis* by 14 to 28 days. The range of concentrations for species other than *M. tuberculosis* was from 0.3 to 1.6 µg/ml. No immunoreactive material was detected in cultures which failed to grow Mycobacteria. Sputum from patients 18-26 failed to grow after decontamination. Prior to decontamination, these sputa contained organisms which are among those listed above. Cultures of the organisms listed contained no detectable immunoreactivity.

Table 2 shows the results of immunoassay of cultures of *M. tuberculosis* and *M. fortuitum* which were initiated as 1:50 dilutions of McFarland 1 cultures.

TABLE 2

Concentration of Immunoreactive PPD in Cultures of *M. Tuberculosis* and Fortuitum.

| Day | *M. tuberculosis* ng/ml | *M. fortuitum* ng/ml |
|---|---|---|
| 1 | <100 | <100 |
| 2 | 120 | <100 |
| 4 | 580 | <100 |
| 5 | 820 | <100 |
| 6 | 1360 | <100 |

During six days of growth, there was a step-wise increase in the immunoreactive PPD measured in cultures of *M. tuberculosis* while no immonoreactive PPD was detected in cultures of *M. fortuitum.* Since the doubling time of *M. tuberculosis* is shown to be approximately 24 hours and the concentration of immunoreactive PPD in the culture medium also doubled at about this rate, the immunoreactivity is a direct measure of the number of organisms. This finding is confirmed by colony counts on 7H10 plates. Antibiotic sensitivity can be determined by measuring the accumulation of immunoreactivity in the presence and absence of inhibiting concentratitons of antibiotics.

SUMMARY AND DISCUSSION

The data presented here indicate that the immunoreactive material being detected is quite specific for Mycobacteria. Although material derived from *M. tuberculosis* reacts more strongly, there is cross-reactivity with other Mycobacterial species. Immunoreactive materials were detected in culture media of all Mycobacterial species studied. No immunoreactivity was detected in culture media from diverse bacterial and fungal species. The accumulation of immunoreactive material in cultures is proportional to the numbers of organisms. The pattern of cross-reactivity appears favorable since it allows identification of Mycobacterial disease caused by a variety of species. The method can be used for diagnosis and for determining the spectrum of antibiotic sensitivity of Mycobacteria.

The obvious need for more rapid methods for the diagnosis of tuberculosis and other Mycobacterial infections brought about by the techniques of the present invention are increased sensitivity, safety of working with autoclaved, non-infectious material and the ability to analyze multiple samples rapidly and at low cost.

Having now fully described this invention, it will be apparent to one of ordinary skill in the art that the same can be carried out with minor modifications which do not effect the content or spirit thereof.

What is claimed as new and intended to be secured by Letters Patent of the United States is:

1. A method for detecting the presence of Mycobacteria in a fluid or tissue which comprises:
   mixing said fluid or tissue containing a secretory product of Mycobacteria with a complex of a tracer-containing molecule, and a binding macromolecule having reversible binding affinity for said tracer-containing molecule, and detecting said tracer containing molecule wherein said tracer-containing molecule is a heat-stable charcoal-adsorbable labeled protein obtained from the growth media of *Mycobacterium tuberculosis*, said protein having a molecular weight of between 20,000 and 30,000, immunochemical stability over a temperature range of 4° C.–250° C., a pH range of 3.0–9.0 and exhibiting comigration towards the anode in the presence of bovine serum albumin and borate buffer at a pH of 8.6 with an applied voltage of 80 volts on starch gel electrophoresis for 12 hours.

2. The method of claim 1, wherein said binding macromolecule is an antibody raised against secretory tubercular protein derived from a bacterium of the genus Mycobacterium.

3. The method of claim 2, wherein said bacterium is *Mycobacterium tuberculosis*.

4. The method of claim 1, wherein said tracer-containing molecule is selected from the group consisting of a radiolabeled molecule, a chromophore labeled molecule and an enzyme-labeled molecule.

5. The method of claim 4, wherein said tracer-containing molecule is a radiolabeled molecule labeled with $^{125}I$.

6. The method of claim 1, wherein said fluid is the biological fluid of a human or non-human animal.

7. The method of claim 6, wherein said fluid is the biological fluid of a human animal.

8. The method of claim 1, wherein said Mycobacteria being detected are selected from the group consisting of *M. tuberculosis, M. intracellulare, M. scrofulaceum, M. simiae, M. bovis, M. leprae, M. avium, M. phlei, M. smegmatis, M. batty, M. kansasii, M. fortuitum, M. africanium, M. ulcerans, M. marinum* and *M. xenopi.*

9. The method of claim 8, wherein said Mycobacteria is *M. tuberculosis.*

10. The method of claim 1, which further comprises determining the susceptibility of Mycobacteria to antibiotic substances by measuring the accumulation of secretory product of Mycobacteria which are growing in the presence of said antibiotic substances.

11. The method of claim 1, which, after mixing said complex with said fluid or tissue, further comprises:

separating tracer-containing molecule which is bound on said binding macromolecule, from tracer-containing molecule which is free therefrom, and then determining the ratio of said bound to said free tracer-containing molecule.

12. The method of claim 11, wherein said separation of said bound tracer-containing molecule from said free tracer-containing molecule is carried out by absorbing said free tracer-containing molecule on the surface of a material having absorption properties therefor.

13. The method of claim 12, wherein said material is selected from the group consisting of charcoal, silicates and hydroxyapatite.

14. The method of claim 13, wherein said material is charcoal.

15. The method of claim 11, wherein said separation of said bound tracer-containing molecule from said free tracer-containing molecule is carried out by adding an antibody raised against said binding macromolecule and thereby precipitating any bound tracer-containing molecule.

16. The method of claim 15, wherein said antibody is attached to an insoluble solid support.

17. The method of claim 11, wherein said separation of said bound tracer-containing molecule from said free tracer-containing molecule is carried out by gel filtration chromatography.

18. The method of claim 11, wherein said separation of said bound tracer-containing molecule from said free tracer-containing molecule is carried out by fractional solvent precipitation.

19. The method of claim 18, wherein said solvent is selected from the group consisting of ethanol, dioxane, polyethylene glycol, trichloroacetic acid, a solution of sodium sulfite, and a solution of ammonium sulfate.

20. The method of claim 1, wherein said binding macromolecule is attached on an insoluble support.

21. The method of claim 20, wherein said insoluble support is a particle of a cross-linked resin.

22. The method of claim 21, wherein said resin is selected from the group consisting of dextran and cellulose.

23. The method of claim 20, wherein said solid support is the interior of a test tube.

24. The method of claim 20, wherein said solid support is a polyolefin disc.

25. The method of claim 20, wherein said binding macromolecule is covalently attached to said solid support.

26. The method of claim 20, which, after mixing said complex with said fluid or tissue, further comprises:

separating tracer-containing molecule which is bound on said binding macromolecule, from tracer-containing molecule which is free therefrom, and then determining the ratio of said bound to said free tracer-containing molecule.

27. The method of claim 1, wherein said detection of said tracer-containing molecule is carried out by scintillation counting.

28. The method of claim 1, wherein said detection of said tracer-containing molecule is carried out by a colorimetric assay.

29. The method of claim 1, which is used for the detection of infectious tuberculosis in humans.

* * * * *